US00PP23767P2

(12) United States Plant Patent
Pieters

(10) Patent No.: US PP23,767 P2
(45) Date of Patent: Jul. 23, 2013

(54) ***CHRYSANTHEMUM* PLANT NAMED 'ESPERO YELLOW'**

(50) Latin Name: *Chrysanthemum×morifolium*
Varietal Denomination: Espero Yellow

(75) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 258 days.

(21) Appl. No.: 13/065,897

(22) Filed: Mar. 31, 2011

(51) Int. Cl.
*A01H 5/00* (2006.01)

(52) U.S. Cl.
USPC ..... Plt./289

(58) Field of Classification Search
USPC ..... Plt./289
See application file for complete search history.

(56) References Cited

PUBLICATIONS

PLUTO Plant Variety Database 2012-06 search for 'Espero Yellow'.*

* cited by examiner

*Primary Examiner* — Annette Para
(74) *Attorney, Agent, or Firm* — C. A. Whealy

(57) ABSTRACT

A new and distinct cultivar of *Chrysanthemum* plant named 'Espero Yellow', characterized by its compact, upright, outwardly spreading and rounded plant habit; freely branching habit; dense and full plant habit; uniform and freely flowering habit; small decorative-type inflorescences with yellow-colored ray florets; and excellent garden performance.

1 Drawing Sheet

Botanical designation: *Chrysanthemum×morifolium*.
Cultivar denomination: 'ESPERO YELLOW'.

BACKGROUND OF THE INVENTION

The present invention relates to a new and distinct cultivar of *Chrysanthemum* plant, botanically known as *Chrysanthemum×morifolium*, and hereinafter referred to by the name 'Espero Yellow'.

The new *Chrysanthemum* is a naturally-occurring whole plant mutation of *Chrysanthemum×morifolium* 'Espero White', not patented. The new *Chrysanthemum* plant was discovered and selected by the Inventor as a flowering plant from within a population of plants of 'Espero White' in a controlled greenhouse environment in Oostnieuwkerke, Belgium in September, 2007.

Asexual reproduction of the new *Chrysanthemum* plant by vegetative cuttings was first conducted in a controlled greenhouse environment in Oostnieuwkerke, Belgium in January, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Espero Yellow'. These characteristics in combination distinguish 'Espero Yellow' as a new and distinct *Chrysanthemum* plant:

1. Compact, upright, outwardly spreading and rounded plant habit.
2. Freely branching habit; dense and full plant habit.

3. Uniform and freely flowering habit.
4. Small decorative-type inflorescences with yellow-colored ray florets.
5. Excellent garden performance.

Plants of the new *Chrysanthemum* differ primarily from the parent, 'Espero White', in ray floret color as plants of 'Espero White' have white-colored ray florets.

Plants of the new *Chrysanthemum* can also be compared to plants of *Chrysanthemum×morifolium* 'PPP TER Y05', disclosed in U.S. Plant Pat. No. 16,959. In side-by-side comparisons conducted in Oostnieuwkerke, Belgium, plants of the new *Chrysanthemum* differed from plants of 'PPP TER Y05' in the following characteristics:

1. Plants of the new *Chrysanthemum* were more rounded than and not as upright as plants of 'PPP TER Y05'.
2. Plants of the new *Chrysanthemum* were not as vigorous as plants of 'PPP TER Y05'.
3. Inflorescences of plants of the new *Chrysanthemum* were more fully double than inflorescences of plants of 'PPP TER Y05'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Espero Yellow' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under conditions and practices which approximate those generally used in commercial *Chrysanthemum* production. During the production of the plants, day temperatures ranged from 25° C. to 30° C. and night temperatures ranged from 15° C. to 20° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Espero Yellow'.

Parentage: Naturally-occurring whole plant mutation of *Chrysanthemum×morifolium* 'Espero White', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; moderately dense.

Plant description:

*Appearance*.—Perennial decorative-type *Chrysanthemum*; compact plant habit with stems upright and outwardly spreading giving a uniformly rounded appearance to the plant; very freely branching habit, about 25 to 30 primary lateral branches develop, each primary lateral branch with multiple secondary branches; pinching enhances lateral branch development; dense and full plant habit; strong and moderately vigorous growth habit.

*Plant height*.—About 50 cm.

*Plant width*.—About 60 cm.

*Lateral branches*.—Length: About 30 cm. Diameter: About 3 mm to 4 mm. Internode length: About 2 cm. Strength: Strong. Texture: Pubescent; longitudinally ridged. Color: Close to 144A.

*Leaves*.—Arrangement: Alternate, simple. Length: About 2.5 cm to 4 cm. Width: About 1.5 cm to 2 cm. Apex: Rounded to cuspidate. Base: Attenuate. Margin: Palmately lobed and serrate, sinuses between lateral lobes divergent to parallel. Texture, upper and lower surfaces: Slightly pubescent. Color: Developing leaves, upper surface: Close to 137C. Developing leaves, lower surface: Close to 137D. Fully expanded leaves, upper surface: Close to N137C; venation, close to 148C. Fully expanded leaves, lower surface: Close to 147B; venation, close to 147B to 147C. Petiole: Length: About 1 cm. Diameter: About 2 mm. Texture, upper and lower surfaces: Slightly pubescent and rough. Color, upper surface: Close to 146C. Color, lower surface: Close to 146D.

Inflorescence description:

*Appearance*.—Decorative-type inflorescence form; inflorescences borne on terminals above foliar plane; disc and ray florets arranged acropetally on a capitulum.

*Fragrance*.—Faintly fragrant, pungent.

*Flowering response*.—Under natural season conditions, plants flower mid-September in Belgium; flowering response time, about six weeks.

*Postproduction longevity*.—Inflorescences maintain good color and substance for about seven weeks in an outdoor nursery; inflorescences persistent.

*Quantity of inflorescences*.—About 20 inflorescences develop per lateral branch.

*Inflorescence bud*.—Height: About 4 mm. Diameter: About 7 mm. Shape: Globular. Color: Close to 137C.

*Inflorescence size*.—Diameter: About 4 cm. Depth (height): About 2 cm. Disc diameter: About 4 mm. Receptacle diameter: About 3 mm. Receptacle height: About 2.5 mm to 3 mm. Receptacle color: Close to 144B.

*Ray florets*.—Length: About 2.5 cm to 4 cm. Width: About 3 mm. Shape: Oval. Apex: Rounded. Base: Attenuate. Margin: Entire. Aspect: Mostly flat. Texture, upper and lower surfaces: Smooth, glabrous. Number of ray florets per inflorescence: About 125 to 150 arranged in about eight whorls. Color: When opening, upper and lower surfaces: Close to 12A. Fully opened, upper and lower surfaces: Close to 6A; color becoming closer to 4A with development.

*Disc florets*.—Length: About 3 mm. Diameter: About 0.5 mm to 1 mm. Shape: Tubular, elongated; apices acute. Number of disc florets per inflorescence: About 60 massed at the center of the inflorescence. Color, immature: Close to 145A. Color, mature: Close to 12A.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 4 cm. Length, fourth peduncle: About 5 cm. Length, seventh peduncle: About 5 cm. Diameter: About 3 mm. Angle: About 30° from vertical. Strength: Moderately strong. Texture: Slightly pubescent. Color: Close to 137C.

*Reproductive organs*.—Androecium: Not observed. Gynoecium: Not observed.

*Seed/fruit*.—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Espero Yellow' as illustrated and described.

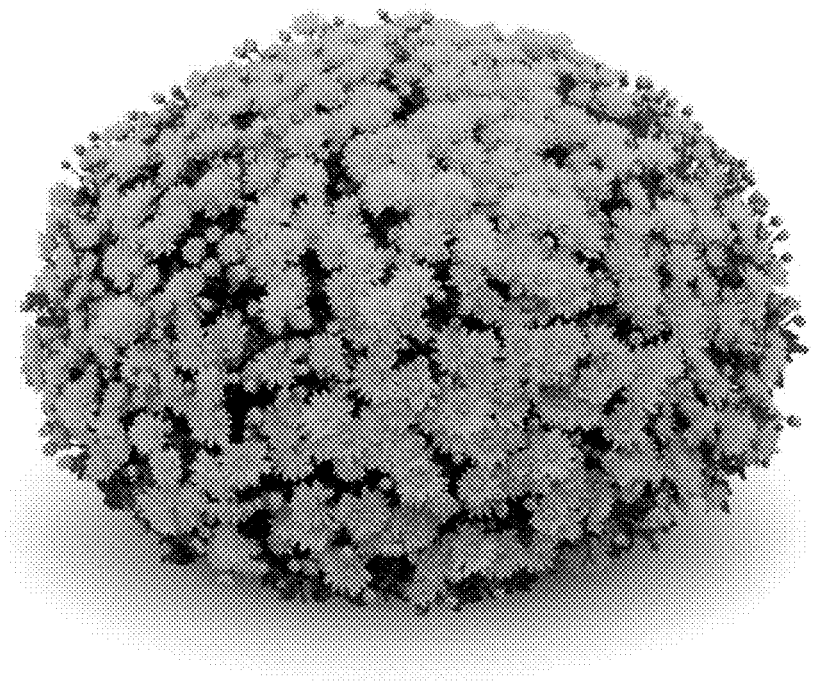

* * * * *